United States Patent [19]
Acker

[11] Patent Number: 5,729,129
[45] Date of Patent: Mar. 17, 1998

[54] MAGNETIC LOCATION SYSTEM WITH FEEDBACK ADJUSTMENT OF MAGNETIC FIELD GENERATOR

[75] Inventor: David E. Acker, Setauket, N.Y.

[73] Assignee: Biosense, Inc., Setauket, N.Y.

[21] Appl. No.: 476,380

[22] Filed: Jun. 7, 1995

[51] Int. Cl.[6] .................. G01B 7/14; G01S 5/04; A61B 5/05
[52] U.S. Cl. .................. 324/207.12; 324/232; 128/653.1
[58] Field of Search .................. 324/232, 207.12, 324/225, 207.17, 207.22, 207.23; 128/653.1, 899

[56] References Cited

U.S. PATENT DOCUMENTS

| | | |
|---|---|---|
| 4,613,866 | 9/1986 | Blood . |
| 4,642,786 | 2/1987 | Hansen . |
| 4,652,820 | 3/1987 | Maresca .................. 324/207.12 |
| 4,710,708 | 12/1987 | Rorden et al. . |
| 4,849,692 | 7/1989 | Blood . |
| 4,945,305 | 7/1990 | Blood . |
| 5,013,987 | 5/1991 | Wakui .................. 324/207.12 |
| 5,042,486 | 8/1991 | Pfeiler et al. . |
| 5,099,845 | 3/1992 | Besz et al. . |
| 5,211,165 | 5/1993 | Dumoulin et al. . |
| 5,251,635 | 10/1993 | Dumoulin et al. . |
| 5,253,647 | 10/1993 | Takahashi et al. . |
| 5,255,680 | 10/1993 | Darrow et al. . |
| 5,265,610 | 11/1993 | Darrow et al. . |
| 5,391,199 | 2/1995 | Ben-Haim . |

FOREIGN PATENT DOCUMENTS

WO 94/04938   3/1994   WIPO .

*Primary Examiner*—Walter E. Snow
*Attorney, Agent, or Firm*—Lerner, David, Littenberg, Krumholz & Mentlik

[57] ABSTRACT

A system for locating objects in space, such as medical instruments within the body of a patient, based upon transmission of magnetic fields from coils in a fixed frame of reference to sensors on the object or visa-versa. The current supplied to the coils is adjusted to assure that the sensors receive fields within a preselected range of magnitudes regardless of the location of the object in space. This assures that the sensor operates within its optimum range, and permits use of compact transmitters and sensors.

22 Claims, 3 Drawing Sheets

MAGNETIC LOCATION SYSTEM WITH FEEDBACK ADJUSTMENT OF MAGNETIC FIELD GENERATOR

FIELD OF THE INVENTION

The present invention relates to systems for determining the location and/or orientation of objects in space by detecting magnetic fields.

BACKGROUND OF THE INVENTION

Various systems have been proposed for detecting the position and/or orientation of an object using magnetic or electromagnetic fields. These systems typically employ field transmitters, such as electromagnet coils, disposed at known locations in a fixed reference frame and a sensor, such as a coil or other transducer mounted to the object to be located. Each transmitter projects a field varying in space in a fixed frame of reference. The pattern of variation in space for each transmitter is different than the pattern for each other transmitter. For example the transmitters may be identical to one another but disposed at different locations or in different orientations. The field patterns of the transmitters are thus displaced or rotated relative to one another and relative to the fixed frame of reference. The sensor on the object detects the parameters of the field prevailing at the location of the object as, for example, the magnitude and/or direction of the field at the object or the magnitudes of individual components of the field at the object in one or more preselected directions. The transmitters may be actuated in a predetermined sequence so that at any time only one transmitter is active and therefore the field prevailing at the object is only the field contributed by one transmitter, plus a background field due to the Earth's magnetic field and other environmental sources. Alternatively, the transmitters can be driven at different frequencies so that components of the signal from the sensor varying at different frequencies represent contributions to the field at the object from different transmitters. Based upon the detected parameters of the fields from the individual transmitters, and the known pattern of variation of the field from each transmitter, a computer system calculates the position and orientation of the sensor, and hence the position of the object bearing the sensor, in the fixed frame of reference of the transmitters. In a variant of this system, the object to be located carries the transmitter or transmitters, whereas a plurality of sensors are disposed at various locations or orientations in the fixed frame of reference. The location and/or orientation of the object is deduced from signals representing the parameters of the field prevailing at the various sensors.

Systems of this general nature are disclosed in U.S. Pat. Nos. 4,849,692; 4,642,786; 4,710,708; 4,613,866 and 4,945,305. Systems according to this general design can be used to provide a three-dimensional spatial input capability for a computer. Another system of this nature is disclosed in International Patent publication WO94/04938. In the '938 publication, the object to be located may be a medical endoscope. Such a system may include a sensor mounted on the tip of an endoscope, so that the location and/or orientation of the endoscope tip can be determined while the sensor is disposed inside the body of a medical patient. This allows the physician to monitor the endoscopic procedure without resorting to a fluoroscopy or other techniques using ionizing radiation to localize the instrument. In one embodiment (pages 26–27), the '938 publication contemplates an arrangement in which plural transmitting coils are actuated simultaneously to "steer" the direction of the resulting field and thereby align the field with the sensor. The '938 publication characterizes this arrangement as undesirable. Other systems for locating medical instruments such as endoscopes and catheters based upon transmitted fields are disclosed in U.S. Pat. Nos. 5,042,486; 5,099,845; 5,211,165; 5,251,635; 5,253,647; 5,255,680; 5,265,610 and 5,391,199.

Systems of this nature typically have used fields having strength which varies as the third power, or a higher power, of distance from the transmitter. There is, accordingly, a very large variation in the strength of each field from location to location. In a medical device locating system, adapted to detect the location of the sensor anywhere within a sensing volume having dimensions on the order of 0.5 to 1.0 m, the field strength may vary through many orders of magnitude from one end of the sensing volume to another. When the sensor and the object to be located happen to be near a particular transmitter, they will receive an extremely strong field, whereas when the sensor and object are at the end of the sensing volume remote from the particular transmitter, they will receive only a very weak field from that transmitter. This requires a sensor with a very substantial dynamic range, capable of accurately monitoring very strong and very weak fields. That, in turn, poses stringent demands on the design of the sensor and may require a larger sensor. Moreover, the signal to noise ratio is poor when monitoring a very weak field and the accuracy of the system is accordingly less than optimum in these conditions. Both of these considerations are particularly important in systems for medical applications, where the sensor must be small to fit inside a medical device such as a catheter or endoscope. Although such systems can provide useful results, further improvement would be desirable. The same problems arise in systems using a coil or other transmitter on the object to be located and plural sensors in the fixed frame of reference. Here again, a particular sensor will be exposed either to a very strong field or a very weak field depending on whether the transmitter is adjacent to or remote from the sensor in question.

Commonly assigned, copending U.S. Pat. No. 08/132,479, filed Oct. 6, 1993, now U.S. Pat. No. 5,558,091, discloses a solution to these problems. Certain preferred embodiments according to the '479 application include electromagnets which are operable to generate a plurality of different magnetic fields. Each field has at least one component with a non-zero magnitude that is either constant, linear or nearly linear with respect to distance in a particular direction within a sensing volume. Such an arrangement provides less variation in field magnitude throughout the sensing volume than a comparable arrangement in which the field strength varies as the third or higher power of distance. Thus, with the quasi-linear fields, the difference between minimum and maximum field within a given sensing volume is substantially smaller. This substantially alleviates the problems discussed above. However, it is not always convenient to use the particular coil arrangements which provide such quasi-linearly varying fields.

SUMMARY OF THE INVENTION

One aspect of the present invention provides apparatus for determining position including field generating means for producing a plurality of magnetic fields. The field generating means is arranged to provide such fields having parameters, such as field strength and/or field direction, varying with location within a sensing volume according to known patterns of variation. The pattern of variation for each field is different than the pattern of variation for each other field. For example, where the field generating means includes a plurality of transmitting coils, the coils are disposed at different locations and/or different orientations relative to the sensing volume. Apparatus according to this aspect of the invention also includes at least one sensor adapted to detect one or more parameters of the field prevailing at the sensor when the sensor is at an unknown location within the sensing volume, and to provide one or more sensor signals representing such detected parameters. For example, the sensor may include a sensor body and a plurality of component sensors disposed on the sensor body, each component sensor being operative to measure the magnitude of a magnetic field component in a preselected local direction relative to the sensor body to provide a component sensor signal representing that particular component of the field prevailing at the sensor. The apparatus further includes calculation means for calculating the location of the sensor, the orientation of the sensor or both based upon the sensor signals and upon the unknown patterns of variation of the fields. The apparatus also includes feedback control means for adjusting the field generating means to alter the known pattern of variation of at least one of the fields responsive to the sensor signals, to the calculated location of the sensor or both so as to maintain the detected parameters of the altered field at the sensor within a preselected range. For example, where the field generating means includes a plurality of transmitters disposed adjacent the sensing volume, the feedback control means can be arranged to increase the strength of the field transmitted by a particular transmitter when the sensor is remote from such transmitter, and to decrease the strength of the field emitted by that transmitter when the sensor is close to the transmitter. Thus, the parameters of the field detected at the location of the sensor will always lie within a relatively narrow range of values. Because the transmitted field is altered in a known manner, the position and/or orientation of the sensor can still be calculated, simply by using the altered field as the basis for calculation. For example, where the feedback control means increases the current flowing to an electromagnetic coil, the parameters used in the calculation to represent the strength of the field emitted from that particular coil are adjusted accordingly.

Apparatus according to this aspect of the present invention can maintain the detected field parameters at the sensor location, such as the magnitude of the field at such location, within a relatively narrow range even where the field strength varies with a power of distance greater than the first power as, for example, where the field strength varies with the third power of distance from the coil. The system therefore can provide good signal to noise ratio, even with a very small sensor. Moreover, there is no need for any particular coil configuration to produce a linear or quasi-linear field. For example, in a medical application, a plurality of individual coils may be disclosed at various locations beneath a patient receiving bed, or on one side of the bed.

Although apparatus according to this aspect of the invention can utilize any type of sensor, it has additional advantages when used with magnetoresistive sensors or other sensors which can lose accuracy when exposed to very high magnetic fields. Because the field is maintained within a relatively narrow range, the sensors are not exposed to fields which would impair their accuracy. In a further variant of the invention, the feedback control system is actuated to maintain the parameters of the field at each sensor within the narrowest attainable range of values. Thus, the feedback control maintains the field parameters at the sensor at substantially constant values. Here again, the transmitted fields are altered in a known manner, and the disposition of the sensor can still be calculated by using the altered fields as the basis for calculation.

A further aspect of the present invention provides apparatus including at least one transmitter adapted for mounting to the object to be located and also including a plurality of sensors disposed adjacent a sensing volume. The apparatus according to this aspect of the invention includes calculation means for determining a calculated location of the transmitter based upon signals from the sensors and upon the known pattern of variation of the field at the transmitter. Here again, feedback control means are provided for adjusting the field generating means to alter the known pattern of variation of field sent by the at least one transmitter in response to the sensor signal, to the calculated location of the transmitter or both so as to maintain the parameters of the field from the at least one transmitter prevailing at each sensor within a preselected range. This arrangement is similar to the arrangement discussed above, except that the transmitter or transmitters are disposed on the object to be located whereas the sensors are located in the fixed frame of reference of the sensing volume. Here again, when the transmitter is close to the sensor, or where the orientations of the transmitter and sensor favor strong coupling between the transmitted field and the sensor, the strength of the field is reduced. If the transmitter is relatively far from the sensor, or in a unfavorable orientation, the control means increases the strength of the transmitted field. This arrangement provides advantages similar to those discussed above.

A further aspect of the invention provides apparatus for sensing the disposition of an object—its position, orientation or both—in a frame of reference. Apparatus according to this aspect of the invention includes transmitter means including at least one transmitter for providing a field and sensor means including at least one sensor for sensing one or more parameters of a field prevailing at each such sensor and providing one or more sensor signals indicative of such parameters. The transmitter means and said sensor means cooperatively define a plurality of transmitter-sensor pairs, each including one transmitter and one sensor as elements of the pair, one element of each such pair being disposed on the object and the other element of each such pair being disposed at a known disposition in said frame of reference. Typically, at least one element of each transmitter-sensor pair is disposed at a different position or orientation than the corresponding element of the other pairs. The apparatus further includes calculation means for determining the disposition of said object based upon said sensor signals feedback control means for adjusting said transmitting means responsive to said sensor signals to thereby maintain at least one of said sensor signals within a preselected range.

Further aspects of the present invention provide methods of determining position and/or orientation wherein the operation of field generating means is altered by feedback control based upon the signals from the sensor, or from the calculated location of the sensor of the transmitter, to maintain the parameters of each field to be detected by each sensor within a preselected range.

Other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
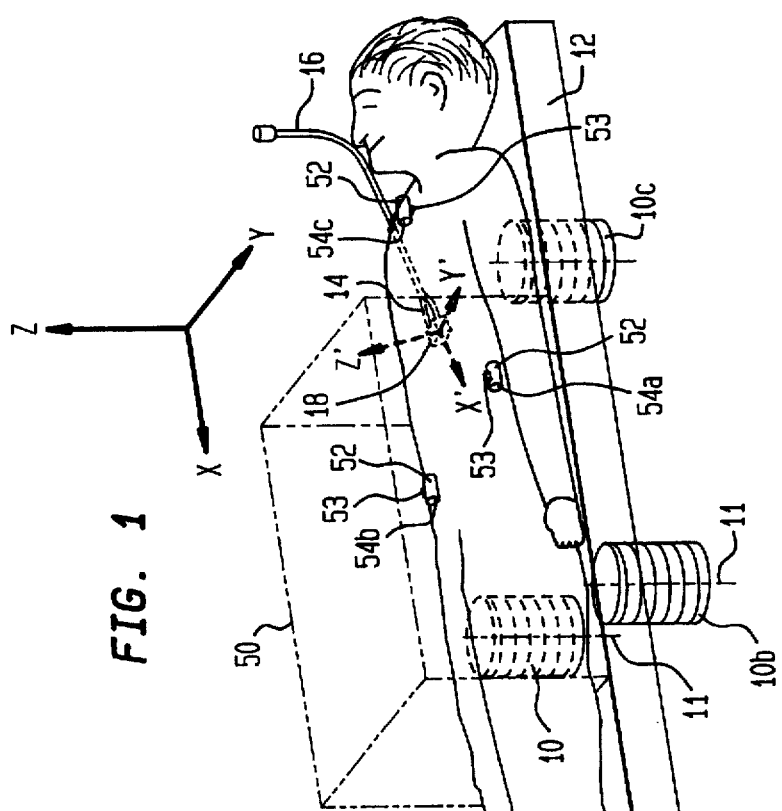
FIG. 1 is a diagrammatic prospective view depicting portions of apparatus in accordance with one embodiment of the invention.
Figure 2:
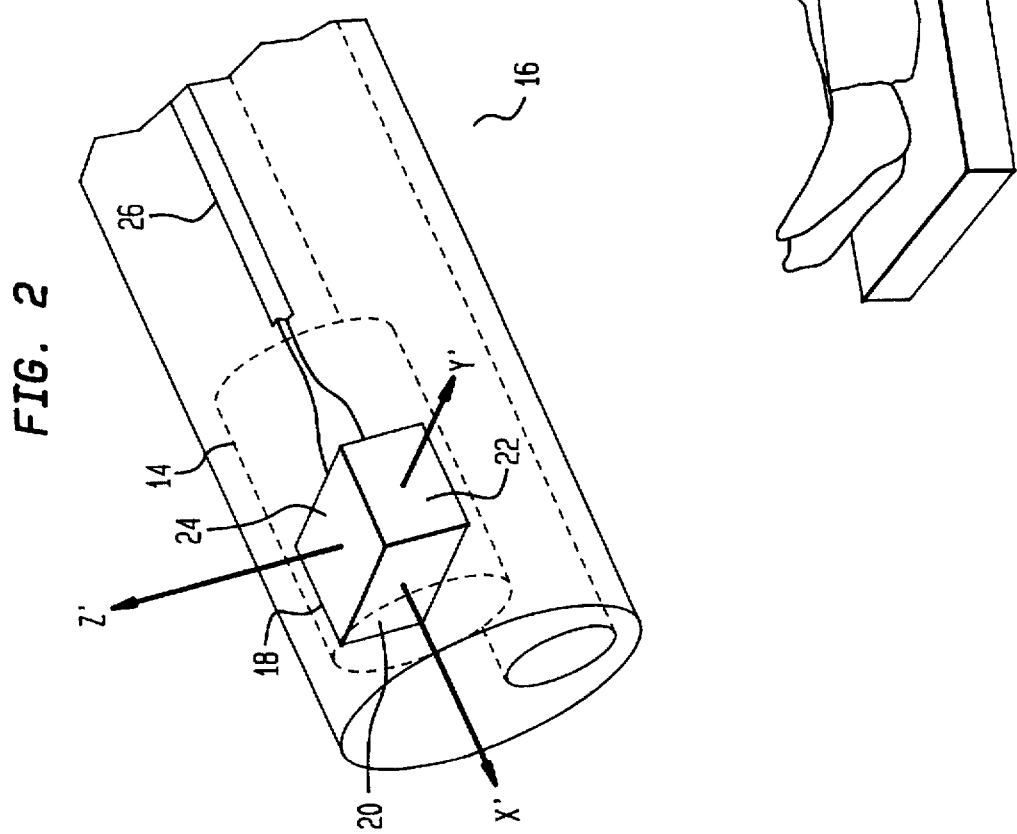
FIG. 2 is a fragmentary, diagrammatic prospective view depicting a portion of the apparatus illustrated in FIG. 1.

Apparatus in accordance with one embodiment of the present invention includes three generally helical transmitter coils 10 disposed in a common plane. Coils 10 are mounted in fixed position in the frame of reference of patient receiving bed 12. That frame of reference is denoted by a Cartesian coordinate system X, Y, Z as shown in FIG. 1. A patient P may be positioned on the patient receiving bed. The axes 11 of the coils are parallel to one another. A patient receiving bed 12 extends just above the plane of coil 10. The apparatus further includes an object or probe 14. The probe is adapted to be inserted into a medical instrument such as a catheter 16 and positioned at a desired location in the catheter, such as at the distal tip of the catheter or at another location along the length of the catheter. Probe 14 has mounted thereon a sensor 18. Sensor 18 includes three component sensors 20, 22 and 24 adapted to sense components of the magnetic field in mutually orthogonal local directions X', Y', and A'. That is, component sensor 20 is sensitive to magnetic fields directed in direction X', but largely insensitive to fields in directions Y' and Z', whereas sensor 22 is sensitive only to fields in direction Y' and sensor 24 is sensitive to fields in direction Z'. These sensors are adapted to provide separate sensor signals representing the separate components. Sensor 18 may be a solid state sensor of the type described in the aforementioned International Patent Publication WO95/09562, the disclosure of which is hereby incorporated by reference herein. As further described therein, each of the component sensors may include a generally planar magnetically sensitive film, such as a magneto-resistive film or a Hall effect sensing film. Each such film may be sensitive to fields directed normal to the plane of the film. Alternatively, sensor 18 may include an array of miniature coils, the axes of the coils being oriented orthogonal to one another. Although these represent the preferred sensors, essentially any other magnetically sensitive device may be employed as, for example, magneto-optical sensors and flux gate magnetometers.

Figure 3:
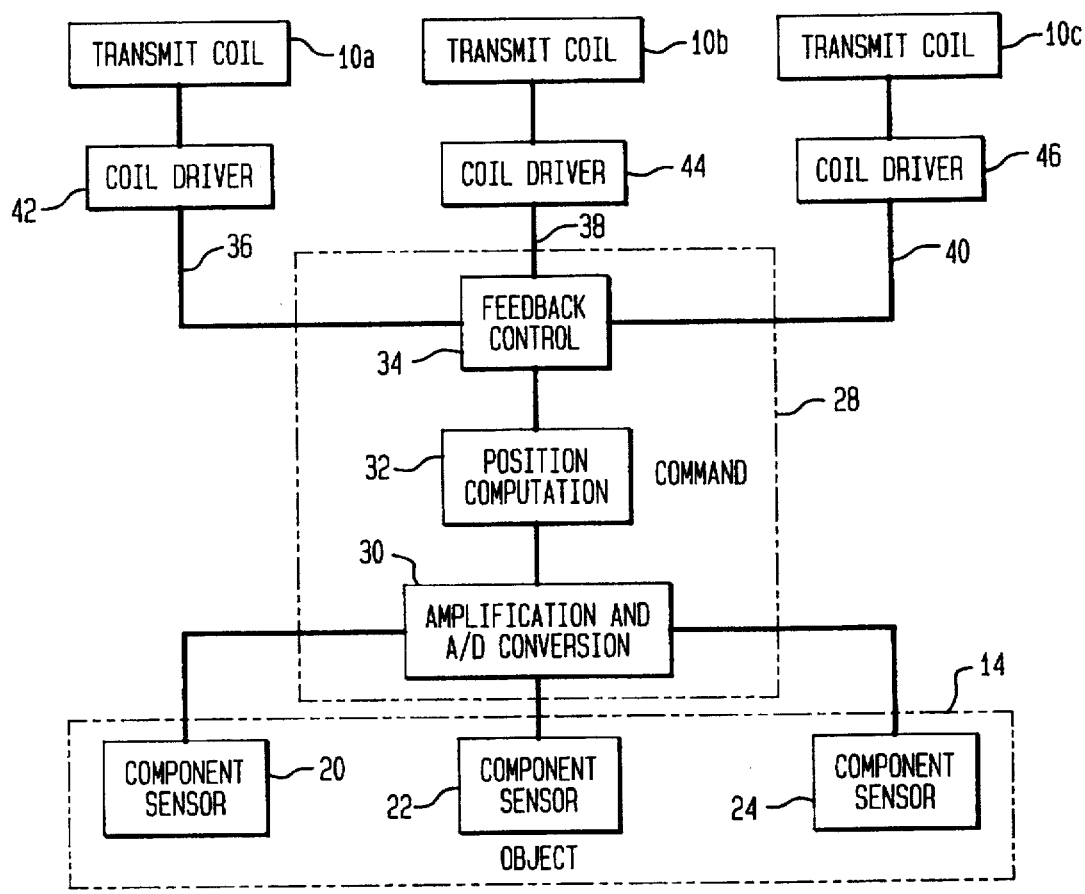
FIG. 3 is a functional block diagram depicting further portions of the apparatus depicted in FIGS. 1 and 2.

Component sensors 20, 22 and 24 are connected through a cable 26, with separate leads for each sensor, to a command unit 28. Command unit 28 (FIG. 3) includes an input amplification and analog to digital ("A/D") conversion section 30 adapted to receive the individual signals from component sensors 20, 22 and 24 of sensor 18, amplify the same and convert the same to digital form. The amplification and A/D conversion unit 30 may also include other conventional signal processing devices such as analog or digital band pass filtering and noise rejection devices and signal averagers. Command unit 28 further includes a computation unit 32. Computation unit 32 may be implemented as a programmed general purpose computer. As further discussed below, the position computation unit is arranged to compute the disposition of sensor 18, and hence the disposition of the object or probe 14 at the catheter tip from the sensor signals. As used in this disclosure, the term "disposition" of an element refers to the position of the element, the orientation of the element or both. Thus, the computation unit is arranged to calculate the position of sensor 18, the orientation of the sensor, or, preferably, both position and orientation. Command unit 28 may be linked to a display device (not shown) for providing a human intelligible representation of the position of the probe or object 14. Such human intelligible representation may be provided either as numerical information presenting the position and/or orientation of object 14 in the X, Y, Z coordinate system or, preferably, as a pictorial representation of the object and of the associated catheter superposed on a pictorial representation of the patient [MOVE THIS UP]. Coils 10 are mounted in fixed position in the frame of reference of patient receiving bed 12. That frame of reference is denoted by a Cartesian coordinate system X, Y, Z as shown in FIG. 1. A patient P may be positioned on the patient receiving bed.

Command unit 28 further includes a control unit 34. Control unit 34 is linked by output lines 36, 38 and 40 to three separate coil drivers 42, 44 and 46. Each coil driver is linked to a separate one of transmitter coils 10. Each coil driver is adapted to send a direct current through the associated transmit coil 10. Each coil driver is arranged to control the amplitude of such current, and to turn the current on or off, in response to control signals received from control unit 34. The control unit is arranged to signal the coil drivers to provide currents to their respective transmit coils in alternating sensitive to magnetic fields directed in direction X', but largely insensitive to sequence, so that coil 10a receives current while coils 10b and 10c are inactive; coil 10b receives current while coils 10a and 10c are inactive and coil 10c receives current while coils 10a and 10b are inactive. The control unit receives data from amplification and conversion section 30 and, as further discussed below, actuates the coil drivers to vary the amplitude of the current to each coil. The control unit may include conventional interface devices such as digital to analog converters or bus interface units so that the output of the control unit is compatible with the control input of each coil driver. Also, although the control unit is illustrated separately from the other logical units of command unit 28, it should be appreciated that the control unit may share physical elements of the command unit and other elements. For example, where the command unit incorporates a general purpose computer, the processor of the computer may serve both as an element of the position computation unit and as an element of the control unit, executing functions appropriate to the different units at different times.

In a method according to one aspect of the invention, an catheter 16 is advanced into the body of a patient P. The probe 14 with sensor 18 thereon is disposed at the tip of the catheter. The catheter tip is disposed at an unknown location somewhere above the plane of coils 10. Control unit 34 actuates the coil drivers in sequence, using an initial or default value for the current amplitude to be provided to each coil 10. Amplification and conversion unit 30 samples the signal from each of the component sensors 20, 22 and 24 at a preselected time after the beginning of current flow through each coil. For example, at a preselected time after the beginning of current flow through transmit coil 10a, unit 30 takes a sample of the signal from each of component sensors 20, 22 and 24, and converts the same to digital format. Command unit 28 then calculates a total field magnitude based upon these individual signals. The total field magnitude is:

$$|B_{10a}| = \sqrt{(k_{20}S_{20})^2 + (k_{22}S_{22})^2 + (k_{24}S_{24})^2}$$

where:

$B_{10a}$ is the magnitude of the magnetic field vector at sensor 18 at the time that coil 10a is actuated;

$K_{20}$ is a sensitivity factor relating the signal strength from sensor 20 to the magnetic field component along axis X';

$S_{20}$ is the signal strength from sensor 20 during the actuation; and $K_{22}$, $S_{22}$ and $K_{24}$ and $S_{24}$ are similar sensitivity constants and signal strengths for the other sensors 22 and 24.

In like manner, the system actuates coils 10b and 10c in order, using the default current strength. Here again, the system computes the magnitude of the total field vector prevailing at the sensor during actuation of coil 10b and independently computes the magnitude of the total field vector prevailing at the sensor during actuation of coil 10c.

Figure 4:
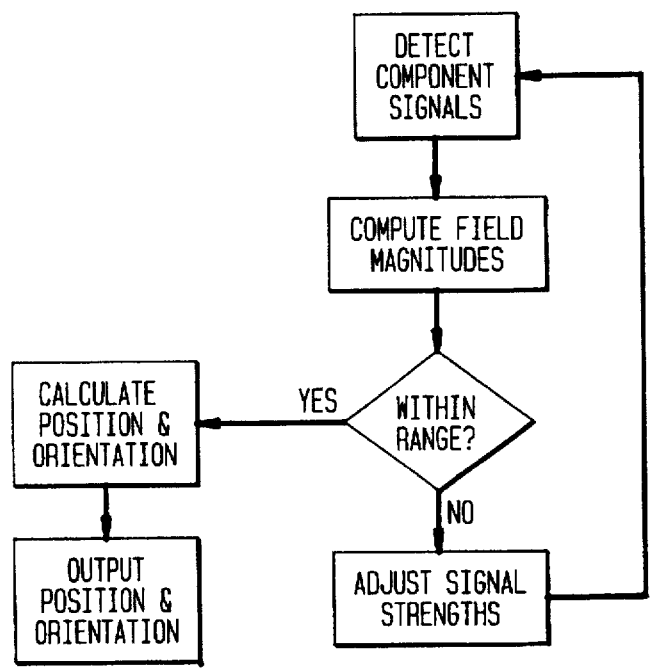
FIG. 4 is a block diagram depicting certain steps in methods according to embodiments of the invention.

As shown in FIG. 4, after detecting the component signals and calculating the total field magnitude prevailing at the sensor during actuation of each coil, the control unit determines whether or not all of the field magnitudes are within a preselected range of magnitudes. This preselected range is chosen to lie within the optimum operating range of sensor 18. Thus, the minimum field magnitude is selected to lie well above the noise threshold of the system and above the minimum sensitivity level of the sensor, where the maximum field level is selected to lie well below the maximum limit of linearity of the sensor, and well below the maximum field which the sensor can tolerate without loss of accuracy. For a typical magneto-resistive sensor, which is most accurate and repeatable when used with fields of less than about 4 Gauss, the preselected range of field magnitudes may be from about 1.0 to about 2.5 Gauss. With typical Hall effect sensors, which are most accurate when used with fields over about 30 Gauss, the preselected range will be above about 30 Gauss. If the three field vector magnitudes observed during actuation of the three units 10a, 10b and 10c all lie within the preselected range, than the system proceeds to calculate the position and orientation of sensor 18, and hence the position and orientation of probe 14 and the associated tip 16 of the catheter using conventional position finding algorithms. For example, the mathematical methods disclosed in U.S. Pat. No. 4,710,708 for finding positions using a multiple transmitting or receiving stations and a multi-axis sensor can be employed. The disclosure of said '708 patent is hereby incorporated by reference herein. Briefly, the magnitude of the fields in each of the local or sensor directions X', Y', Z' represented by each of the component sensor signals from each of the component sensors 20, 22 and 24 is a function of the overall strength of the field from the coil (also referred to as the magnetic dipole moment of the coil), the distance from the particular coil to the sensor and the sensor rotation angles, i.e., the angles between the local directions X', Y' and Z' and the coil frame of reference directions X, Y and Z. When three component sensor readings are collected during actuation of three separate coils and equated with the component strength, expressed as a function of location for fields from a particular coil, they form a system of nine equations with six unknowns (the X, Y, Z location of the sensor and the three rotation angles). The derivation of these equations is set forth in Appendix A. That system of equations can be solved by iterative methods such as the method of Marquardt or the method of Broyden for least-squares solution of an overdetermined system of non-linear equations. The command unit then provides output indicating the position and orientation of the sensor and hence indicating the position and orientation of probe 14 and of the distal tip of the catheter.

If one or more of the field magnitudes is out of the preselected range, the system does not calculate the position and orientation. Instead, control unit 34 changes the field strength of the coil or coils associated with the out-of-range field strength. For example, where probe 14 and sensor 18 are relatively close to coil 10a, the total field magnitude detected when coil 10a is actuated will be above the preselected range. Control unit 34 therefore will command coil driver 42 to reduce the current to coil 10a on the next actuation cycle. Conversely, if the probe and sensor are relatively far from coil 10c, the field magnitude sensed during actuation of coil 10c with the default of current value will be below the preselected range. Control unit 34 therefore will instruct coil driver 46 to increase the current to coil 10c on the next actuation cycle. The coil drivers may be arranged to vary the overall field strength or dipole moment of each coil stepwise, as by varying the current stepwise. Each increase or decrease commanded by control unit 34 may be one step. Alternatively, the control unit can calculate an increase or decrease proportional to the degree to which the total field magnitude deviates from a target value within the preselected range. Thus, a relatively large change can be made when the field magnitude is far outside of the range, whereas a smaller change can be employed when the field magnitude is close to the range or within the range. The correction process continues until all field strengths are within the preselected range, whereupon the system calculates position and orientation. After the system finds values of coil currents which produce field magnitudes within the range, subsequent actuation cycles use these currents. During operation, as the physician utilizes catheter 16, the position of the catheter tip, and hence the position of probe 14 and sensor 18 may change. Any such change may bring one or more of the field magnitudes outside of the preselected range, whereupon the system will readjust the currents to the coils once again.

As the feedback control unit readjusts the currents to the coils, the altered values of current are translated into new values for field strengths from the individual coils which are used in the aforementioned position determining equations. In this manner, the system assures that the sensor is always exposed to a field having a magnitude within the preselected range wherever the sensor is placed within a sensing volume 50 extending over a preselected region above the plane of coils 10. The exact size of sensing volume 50 will depend upon the breadth of the preselected field magnitude range and the dynamic range of coil drivers 42, 44 and 46, i.e., the degree to which the coil drivers can vary the currents. The size of sensing volume 50 within which the sensor will receive fields within the preselected field magnitude range from all coils will also depend upon the positions of the coils. However, for a typical system having three coils spaced at vertices of an equilateral triangle with sides about 40 cm long, the sensing volume includes a region extending upwardly about 60 cm from the plane of the coils. At the plane of the coils, the sensing volume extends about 20 cm beyond the equilateral triangle bounded by the coils.

In the description set forth above, only one sensor is employed to determine the position and location of only one object. However, plural objects and plural sensors may be utilized. As described in the aforementioned International Publication WO95/09562, a plurality of fiducial markers may be utilized. Each fiducial marker may include a sensor body 52, a tag 53 and a sensor 54 of the same type as sensor 18 releasably connected to the sensor body. The amplification and converson unit 30 is connected to each of these additional sensors in the same manner as to sensor 18. The tag of each sensor may be affixed to the body of the patient, and an image of the patient may be acquired using any imaging method which will show the desired structures of the patient's body and which will also show the tags 53 as, for example, magnetic resonance imaging (MRI), X-ray, CAT scanning or the like. Thus, the tags are constructed to facilitate imaging in the desired imaging method. Where X-ray imaging is used, the tag may be radioopaque; where MRI imaging is used, the tag may include a material which has magnetic resonance response readily distinguishable from that of bodily tissue. Ordinarily, the image is acquired prior to use of the catheter and probe discussed above. The sensors 54 typically are not present in the imaging step. After the imaging step, the sensor bodies 54 and sensors of the fiducial markers are attached to the patient's body at the positions of the tags. When the catheter is employed, sensor signals from sensor 18 on the probe in the catheter are acquired concurrently with signals from the sensor 52 on the fiducial markers. The system determines the location and orientation of sensor 54, and hence of fiducial markers 52 using magnetic fields from coils 10 in the same manner as the system determines the position and orientation of sensor 18 and probe 14. The acquired position and orientation of the fiducial markers 52 can be used to register the previously acquired image of the patient with the position and orientation data for sensor 18 and probe example, where the position and orientation data for the sensor 18 and probe 14 are displayed as a pictorial image of the catheter tip 16 on a screen, the position and orientation of fiducial markers, as determined by the magnetic field locating method can also be displayed. The previously acquired image data may be displayed as a pictorial representation of the patient's structures and that representation will also include a picture of the tags 53. The previously acquired images of the tags are brought into registration with the images of the fiducial markers derived from magnetic location by transforming one or the other image until the picture of the tags in the previously acquired image overlies the representation of the fiducial marker in the magnetically acquired image. Such registration can be achieved by manually adjusting inputs to an image display system while visually matching the displayed images, as described in the aforementioned '562 International Publication or else by automatic calculation of the transformation and rotation parameters necessary to bring the images into registration. Such parameters can be calculated by equating the positions of three or more fiducial marker sensors in the magnetic location frame of reference (the X,Y,Z coordinates of FIG. 1) with the positions of the tags 53 in the image frame of reference as modified by a matrix of unknown rotations a further matrix of unknown transformations. As further described in Appendix B, the resulting matrix equation yields an overdetermined system of nonlinear equations which include the rotation angles and transformation distances. When the images are properly registered, the position of the catheter tip is displayed in true location and orientation relative to the patient's internal structures. In similar fashion, a greater number of fiducial markers, or more than one medical instrument may be located.

In a system using multiple sensors, such as sensors 18 and 54, the coils may be operated in separate cycles so as to provide each sensor with fields having magnitudes in the preselected range appropriate for the sensor. For example, control unit 34 may actuate the coil drivers 42, 44 and 46, and hence transmitting coils 10, in first, second, third and fourth cycles. During the first cycle, the signals from sensor 18 are acquired and the signals from sensors 54 of the fiducial markers are ignored. During the first cycle, the coil currently is adjusted to yield field magnitudes at sensor 18 within the preselected range as discussed above. During the second cycle, the signals from the sensor 54a of a first fiducial marker are acquired, the signals from sensor 18 and the other fiducial marker sensors 54b, 54c are ignored and the coil currents are adjusted to provide a field magnitude at sensor 54a within its preselected range. In the third cycle, the signals from sensor 54b are acquired whereas the other signals are ignore; in the fourth cycle, the signals from sensor 54c are acquired and others are ignored. The cycles may be sequential, with the entirety of a first cycle being performed before the entirety of a second cycle. The cycles may also be interspersed with one another. For example, coil driver 42 can be actuated first to provide a current appropriate to yield the proper field at the first sensor 18 and then can be actuated to provide the appropriate fields at the fiducial marker sensors 54a, 54b and 54c in succession, followed by a similar multiple actuation of the other coils. Likewise, where more sensors are employed, there may be as many separate cycles of operation as sensors. Alternatively, if some of the sensors are known to be close to one another, or if the data from some sensors is less critical than the data from other sensors, the number of cycles may be less than the number of sensors. Thus, the currents used on a given cycle may be adjusted to provide fields within the desired range of magnitude for one sensor. Signals from other sensor can be acquired during this cycle, although such other sensor may encounter a field outside the preselected range. In some cases, the coil currents are fixed for some cycles and adjusted for others. For example, where numerous fiducial markers are employed, it may be possible to achieve acceptable registration accuracy using fixed coil currents to provide the fields when data is acquired from the fiducial markers, whereas the coil currents may be adjusted in the manner discussed above when data is acquired from the sensor in the active device or catheter.

Certain sensors tend to lose accuracy when exposed to magnetic fields above a predetermined maximum. For example, certain magneto-resistive sensors temporarily lose accuracy if exposed to magnetic fields above about 4 Gauss. Where such sensors are employed in a multi-sensor system, the system should have appropriate provisions to avoid exposing sensors to excessive fields. For example, if sensor 54a is disposed close to coil 10b, whereas sensor 18 is disposed remote from coil 10b, sensor 54a may be exposed to extremely high field levels if the system adjusts the current in coil 10b to the level required to generate the appropriate field at sensor 18. To avoid this condition, the data from all sensors can be acquired during all of the cycles, and control unit 34 can be arranged to increase coil currents in a progressive manner over several cycles when an increase is required. The data from sensors which are not used for position monitoring on a particular cycle can be used to inhibit further increases if the field at the nominally unused sensor is approaching dangerous levels. Thus, if the system is in the process of progressively increasing the coil current in coil 10b to provide an adequate field level at sensor 18, the system may terminate such increases if the field magnitude at second sensor 54a during the reading cycle associated with first sensor 18 reaches the maximum level allowed at the second sensor. If this condition occurs while the field level at first sensor 18 is still below the preselected range, the system may display an error message or else may attempt to calculate position and orientation based on out-of-range sensor signal, or both. Alternatively, if the accuracy of the sensor can be restored, the data from the nominally unused sensors can be used to initiate restoration. For example, certain magnetoresistive sensors use a biasing magnetic field. If exposed to excessive fields, such sensors can be reset and restored to accuracy after the excess field is removed by adjusting a bias magnetic field applied within the sensor. The command unit may be arranged to trigger the reset process for one sensor if it is exposed to excess field during a cycle associated with another sensor.

In the foregoing discussion, the coils are driven alternately in a time-multiplexed arrangement. Frequency domain multiplexing can also be employed. Thus, each coil can be actuated with a driving current having a different carrier frequency, and such actuation can be substantially continuous. The signals from sensor 18 will include components varying at the different carrier frequencies, which can be segregated by analog or digital filtering methods. Thus, the signals from component sensor 20, 22 and 24 varying at the carrier frequency of coil 10a can be used to calculate the total field magnitude attributable to coil 10a. That value in turn can be used to trigger feedback control unit 34 to adjust the current to coil 10a. The currents in the other coils can be adjusted in similar manner using the components varying at their respective carrier frequencies. The frequency division multiplexing approach can be extended to multiple sensors. For example, each coil can be driven at a multiple carrier frequencies, equal to the number of sensors, the carrier frequencies for each coil being different from one another and different from all of the other carrier frequencies for all of the other coils. The components in the signals from the first sensor varying at the respective first carrier frequencies can be detected and the strength of the coil currents at the respective first carrier frequencies can be adjusted accordingly, so that the field magnitudes at the first carrier frequencies prevailing at sensor 18 will be within the desired range. In this stage of the process, the components varying at the other carrier frequencies are ignored. The process is reversed with respect the fiducial marker sensor 54a. This approach can be extended to greater numbers of sensors. Also, the frequency multiplexing and time multiplexing approaches can be combined. Thus, each coil can be driven at only one carrier frequency. During a first cycle, first sensor 18 is actuated and the components varying at all of the carrier frequencies are monitored. The coil currents are adjusted accordingly to bring the fields at each carrier frequency into the desired range. During a second cycle, the second sensor 54a (the first fiducial marker sensor) is used and the coil currents are adjusted in the same manner, and so on with the other fiducial marker sensors.

In a further variant, the coil currents, and hence the strengths of the fields from the individual transmitters, can be adjusted to bring the field components detected by each individual component sensor to within a preselected range. In such a system, each coil is adjusted separately with respect to each component sensor. In a first cycle, the current to transmit coil 10a is adjusted to bring the individual sensor signal from component sensor 20, representing the field component magnitude in the local X' direction, into a preselected range. During this cycle, the signals from the other component sensors 22 and 24 are disregarded. In the next cycle, coil 10a is readjusted to bring the field component in the wide prime direction into a preselected range and thus bring the signal from Y prime direction component sensor 22 into the optimum range. The same coil 10a then brings the field component in local direction Z' into a preselected range, and the signal from the prime direction component section 24 is monitored. This sequence of operations is then repeated again for each of the other transmitter coils. This approach can be extended to plural sensors, each having plural component sensors. Here again, the system keeps track of the coil current magnitudes used to produce the fields since by each component sensor. The coil current is reflected in the coil dipole moment (overall field strength) terms of the simultaneous equations.

Where the local direction associated with a particular component sensor is orthogonal, or nearly orthogonal, to the direction of the field produced by a particular coil at the sensor, it may be impossible to bring the component in that local direction into the preselected range without either exceeding the current capacity of the coil driver or producing a total field so strong as to impair one of the other sensors. In this instance, however, at least one of the other component sensors will receive a component having a magnitude in the preselected range of magnitudes. In this variant, the signal from all of the component sensors may be monitored during a cycle associated with a particular component sensor. The maximum current applied to the coil may be limited to avoid exposing any other unused component sensor to an excessive field component in its sensing direction.

In a further variant of this approach, the preselected range of magnitudes for the field component in any particular direction is narrowed to include only a single preselected value, preferably within the optimum range of accuracy of the particular component sensor. The feedback control system thus operates to adjust the coil currents until the field component magnitude is at such single value. The position and orientation are calculated in the same way as discussed above. This variant has the advantage that nonlinearity in the component sensor response cannot affect the accuracy of the system. Provided that it is known that a particular reading from the sensor corresponds to the preselected value of field component magnitude, deviation from a linear relationship between component magnitude and sensor reading at other values of the component magnitude will not impair the accuracy of the system.

Certain field sensors exhibit so-called "off-axis sensitivity". That is, the transfer function or relationship between field component magnitude along the sensitive axis of a particular component sensor and the reading from that component sensor varies when a strong field component orthogonal to such axis is present. Off-axis sensitivity can be corrected by using the readings from two component sensors to evaluate the magnitude of the field perpendicular to the sensitive axis of the third component sensor, and using that magnitude to determine a correction factor to be applied to the reading from the third component sensor.

In the system described above, when the coils are driven with direct current, amplification and conversion unit 30 samples the data from each component sensor at a preselected delay time after the inception of the current. In a variant of this system, the command unit adjusts the delay time from inception of the current to sampling depending upon the current applied in a particular actuation. After inception of the current, the current gradually rises to its steady state value, and hence the overall field strength or dipole moment likewise rises gradually. The changing field induces eddy currents in electrically conductive materials which may be present in or near the sensing volume. These currents induce additional magnetic fields, which can induce erroneous sensor readings. The eddy currents decay when the rate of change in the field slows, as the field approaches its steady state value. The delay time should be long enough for the current to rise to an appreciable portion of its steady state value, and long enough for eddy currents to dissipate sufficiently that they do not cause appreciable errors. The required delay time is less with smaller field magnitudes.

Figure 5:
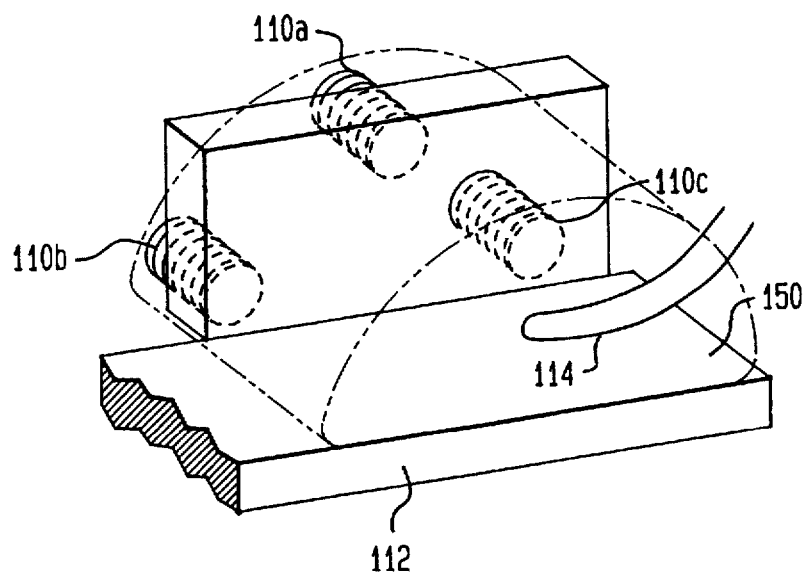
FIGS. 5 and 6 are a diagrammatic perspective view depicting portions of apparatus in accordance with a further embodiment of the invention.
Figure 6:
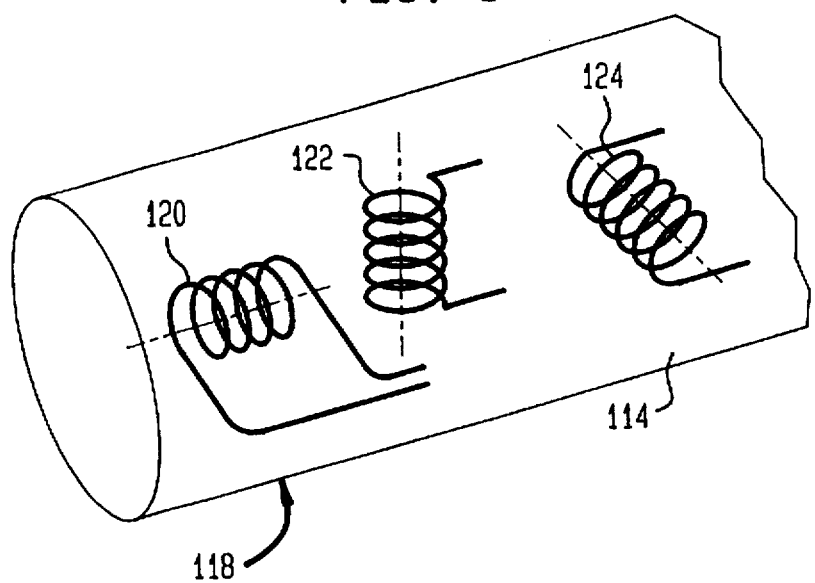

The system illustrated schematically in FIGS. 5 and 6 is similar to that discussed above, except that the roles of the transmitter and sensors are reversed. That is, the probe or object 114 to be tracked is equipped with a transmitters 118 incorporating three miniature coils 120, 122 and 124 disposed on mutually orthogonal axes. These are linked to a control system and coil drivers (not shown) similar to those discussed above with reference to FIG. 3. The fixed reference frame system has three undirectional sensors 110a, 110b and 110c mounted in fixed position relative to the patient receiving bed 112. The sensors are mounted in a common plane. The common plane of the sensors extends generally vertically on one side of the patient receiving bed. The sensing volume 150 extends outwardly from the common plane of the sensors, above the patient receiving bed.

This system can be used in essentially the same manner as the system discussed above. Here again, the current delivered to each coil, and hence the dipole moment of the transmitted field associated with each coil is adjusted so that the magnitude of the field component in the sensing direction of each sensor prevailing at each sensor is within a preselected range of magnitudes.

Numerous combinations and variations of the features discussed above can be utilized without departing from the present invention. By way of example, the transmitting coils 10 of FIG. 1 can be disposed in a vertical plane arrangement as illustrated for the sensors in FIG. 5. Also, the number of transmitters and sensors can be varied. For example, as disclosed in the aforementioned International Publication WO94/04938, the system may include a sensor having three mutually orthogonal sensing axes and a set of three mutually orthogonal transmitting coils having a common center in the fixed frame of reference. Alternatively, the system may include a single uniaxial transmitting coil on the object to be located and three sets of sensors on the affixed frame of reference, each such sensor set incorporating three receiving coils or component sensors adapted to detect fields in a mutually orthogonal direction. The reciprocal arrangement—with three sets of mutually orthogonal transmitting coils and a single uniaxial sensor on the object to be tracked—is also usable. In general, the sensors and transmitters should define a plurality of transmitter-receiver pairs, each including one element on the object and one element on the fixed frame of reference.

In a further variant, the system adjusts the output of the transmitters in response to the calculated disposition of the object being tracked, rather than directly in response to the component signals or total field magnitude signal. Thus, the system can initially operate with the default of current values; derive an initial reading of the position and orientation of the object and then use that initially determined position and orientation to calculate the desired setting for each coil to achieve the desired field levels at the sensor. Such desired setting is selected to yield the field within the desired magnitude range at the object, assuming that the object has the position and orientation found in the initial reading. On the next cycle, the so-calculated coil currents are utilized and the process is repeated. In a variant of this approach, the system can store a lookup table listing the appropriate coil currents for various combinations of object position and orientation. Using the initially determined position and orientation, the system retrieves appropriate coil-current values from the lookup table for use in the next cycle.

In the embodiments discussed above, the sensor is associated with a catheter. The same system can be used with other medical instruments as, for example, endoscopes and surgical instruments. The system can also be applied to determine the disposition of objects other than medical instruments. For example, it can be used in tracking a an input device for a computer.

As these and other variations and combinations of the features described above can be utilized without departing from the invention, the foregoing description of the preferred embodiments should be taken by way of illustration rather than by way of limitation of the invention as defined by the claims.

Appendix A: Calculation of Position and Orientation

Provided that we know the physical configuration of the field generator (transmitter) which is fixed in position during operation, the magnetic field detected by a sensor is a function of the position and orientation of the sensor. In our system field generator coils are stimulated sequentially. The field sensed by a sensor (3 component sensors per probe) can be expressed in terms of position in x, y, z and orientation $\alpha$, $\beta$, $\gamma$ (roll, pitch and yaw respectively) i.e.:

$$B[\text{sensor}][\text{coil}] = f[\text{sensor}][\text{coil}](x, y, z, \alpha, \beta, \gamma)$$

Where [sensor] designates a particular sensor and [coil] designates a particular transmitter coil.

If the real field the sensor measures when [coil] is on is B'[sensor][coil], then theoretically, $$B'[\text{sensor}][\text{coil}] = B[\text{sensor}][\text{coil}]$$

i.e., $$B'[\text{sensor}][\text{coil}] - f[\text{sensor}][\text{coil}](x, y, z, \alpha, \beta, \gamma) = 0.0$$

Since we have 3 sensors and 3 coils, the total equations are 9 with 6 unknowns (x, y, z for probe space location, $\alpha$, $\beta$, $\gamma$ for its orientation). By applying non-linear least square method, we can find unique x, y, z, $\alpha$, $\beta$, $\gamma$ for the probe.

Above shows the general ideal of the algorithm. In detail:

Assume the orthogonal X,Y,Z reference coordinate system (magnetic location Cartesian coordinate) is described by matrix $$e_l = \begin{bmatrix} e_{l11} & e_{l12} & e_{l13} \\ e_{l21} & e_{l22} & e_{l23} \\ e_{l31} & e_{l32} & e_{l33} \end{bmatrix}$$

the probe's orthogonal system is:

$$e_p = \begin{bmatrix} e_{p11} & e_{p12} & e_{p13} \\ e_{p21} & e_{p22} & e_{p23} \\ e_{p31} & e_{p32} & e_{p33} \end{bmatrix}$$

and, since the three sensors on probe may not be orthogonal to each other, their non-orthogonal axes can described as:

$$e_n = \begin{bmatrix} e_{n11} & e_{n12} & e_{n13} \\ e_{n21} & e_{n22} & e_{n23} \\ e_{n31} & e_{n32} & e_{n33} \end{bmatrix}$$

a transfer matrix T[i][j] which is to be used in later on calculation can be obtained from:

$$T_{[i][j]} = e_{n[i]} \cdot e_{p[j]} \quad \forall i, j \in \{1,2,3\}$$

another matrix ortho__OV[i][j] which is to be used also can be defined as:

ortho_$OV_{i[i][j]}=e_{i[i]} \cdot e_{i[j]} \forall i,j \in \{1,2,3\}$ since we use roll($\alpha$), pitch($\beta$), yaw($\gamma$) to define probe orientation, ortho_$OV[i][j]$ can be also described by:

ortho_$OV[1][1]$=cos ($\alpha$) cos ($\beta$)−sin ($\alpha$) sin ($\beta$) sin ($\gamma$)

ortho_$OV[1][2]$=cos ($\alpha$) sin ($\gamma$)−sin ($\alpha$) sin ($\beta$) cos ($\gamma$)

ortho_$OV[1][3]$=−sin ($\alpha$) cos ($\beta$)

ortho_$OV[2][1]$=−cos ($\beta$) sin ($\gamma$)

ortho_$OV[2][2]$=cos ($\beta$) cos ($\gamma$)

ortho_$OV[2][3]$=sin ($\beta$)

ortho_$OV[3][1]$=sin ($\alpha$) cos ($\gamma$)+cos ($\alpha$) sin ($\beta$) sin ($\gamma$)

ortho_$OV[3][2]$=sin ($\alpha$) sin ($\gamma$)−cos ($\alpha$) sin ($\beta$) cos ($\gamma$)

ortho_$OV[3][3]$=cos ($\alpha$) cos ($\beta$)

orthogonal vector matrix can therefore be calculated by matrix multiplication of previous defined matrix T and ortho_OV:

$$ov = T * \text{ortho\_}OV$$

The theoretical magnetic field for an orthogonal system generated at sensor position pointing to $e_{i[i]}$ direction can be expressed as:

$f[\text{coil}][i](x,y,z,\alpha,\beta,\gamma)$ (detail abbreviated), where f is a known function, and includes a dipole moment term having magnitude proportional to the current flow in the particular coil.

After non_orthogonality correction (sensors may not be perpendicular to each other), the magnetic field sensor measures should be:

$$B[\text{sensor}][\text{coil}] = \sum_{i=1}^{3} f[\text{coil}][i](x,y,z,\alpha,\beta,\gamma) \times o \, v^{-1}[i][\text{sensor}]$$

Assume the real field sensor detected when coil is on is B'[sensor][coil], then:

$B'[\text{sensor}][\text{coil}] - B[\text{sensor}][\text{coil}] = 0.0$ therefore, the 9 equations to be solved for x, y, z, $\alpha$, $\beta$, $\gamma$, are:

$B'[\text{sensor1}][\text{coil1}] - \sum_{i=1}^{3} f[\text{coil1}][i](x,y,z,\alpha,\beta,\gamma) \times o \, v^{-1}[i][\text{sensor1}] = 0.0$ $B'[\text{sensor1}][\text{coil2}] - \sum_{i=1}^{3} f[\text{coil2}][i](x,y,z,\alpha,\beta,\gamma) \times o \, v^{-1}[i][\text{sensor1}] = 0.0$ $B'[\text{sensor1}][\text{coil3}] - \sum_{i=1}^{3} f[\text{coil3}][i](x,y,z,\alpha,\beta,\gamma) \times o \, v^{-1}[i][\text{sensor1}] = 0.0$ $B'[\text{sensor2}][\text{coil1}] - \sum_{i=1}^{3} f[\text{coil1}][i](x,y,z,\alpha,\beta,\gamma) \times o \, v^{-1}[i][\text{sensor2}] = 0.0$ $B'[\text{sensor2}][\text{coil2}] - \sum_{i=1}^{3} f[\text{coil2}][i](x,y,z,\alpha,\beta,\gamma) \times o \, v^{-1}[i][\text{sensor2}] = 0.0$ $B'[\text{sensor2}][\text{coil3}] - \sum_{i=1}^{3} f[\text{coil3}][i](x,y,z,\alpha,\beta,\gamma) \times o \, v^{-1}[i][\text{sensor2}] = 0.0$ -continued $B'[\text{sensor3}][\text{coil1}] - \sum_{i=1}^{3} f[\text{coil1}][i](x,y,z,\alpha,\beta,\gamma) \times o \, v^{-1}[i][\text{sensor3}] = 0.0$ $B'[\text{sensor3}][\text{coil2}] - \sum_{i=1}^{3} f[\text{coil2}][i](x,y,z,\alpha,\beta,\gamma) \times o \, v^{-1}[i][\text{sensor3}] = 0.0$ $B'[\text{sensor3}][\text{coil3}] - \sum_{i=1}^{3} f[\text{coil3}][i](x,y,z,\alpha,\beta,\gamma) \times o \, v^{-1}[i][\text{sensor3}] = 0.0$ A well-known non-linear least squares equation solver can be applied to solve the above equations and find probe position x, y, z and orientation $\alpha$, $\beta$, $\gamma$.

Appendix B: Registration of Fiducial Markers

Assumption:

We know the coordinates of three fiducial points in image data (MR etc.) coordinate system (image position):

$\{(Mx1, My1, Mz1), (Mx2, My2, Mz2), (Mx3, My3, Mz3)\}$ and the coordinates of the same three fiducal points in the X,Y,Z, coordinate system of the fixed frame of reference of the magnetic locating apparatus:

$\{(Px1, Py1, Pz1), (Px2, Py2, Pz2), (Px3, Py3, Pz3)\}$ fiducial points $\{(x1, y1, z1), (x2, y2, z2), (x3, y3, z3)\}$ can be formed by $\{(a1, b1, c1), (a2, b2, c2), (a3, b3, c3)\}$ through rotation R and translation T. The rotation matrix R is:

$$R = \begin{bmatrix} Rxx & Ryx & Rzx \\ Rxy & Ryy & Rzy \\ Rxz & Ryz & Rzz \end{bmatrix}$$

where $Rxx$=cos ($\alpha$)×cos ($\gamma$)−sin ($\alpha$)×sin ($\beta$)×sin ($\gamma$)

$Rxy$=cos ($\alpha$)×sin ($\gamma$)+sin ($\alpha$)×sin ($\beta$)×cos ($\gamma$)

$Rxz$=−sin ($\alpha$)×cos ($\beta$)

$Ryx$=−cos ($\beta$)×sin ($\gamma$)

$Ryy$=cos ($\beta$)×cos ($\gamma$)

$Ryz$=sin ($\beta$)

$Rzx$=sin ($\alpha$)×cos ($\gamma$)+cos ($\alpha$)×sin($\beta$)×sin($\gamma$)

$Rzy$=sin ($\alpha$)×sin ($\gamma$)−cos ($\alpha$)×sin ($\beta$)×cos ($\gamma$)

$Rzz$=cos ($\alpha$)×cos ($\beta$)

The translation matrix T is:

$$T = \begin{bmatrix} x & y & z \\ x & y & z \\ x & y & z \end{bmatrix}$$

The relationship between image position and magnetic location apparatus frame of reference position is:

$$\begin{bmatrix} Mx1 & My1 & Mz1 \\ Mx2 & My2 & Mz2 \\ Mx3 & My3 & Mz3 \end{bmatrix} R+T = \begin{bmatrix} Px1 & Py1 & Pz1 \\ Px2 & Py2 & Pz2 \\ Px3 & Py3 & Pz3 \end{bmatrix}$$

or $$\begin{bmatrix} Mx1 & My1 & Mz1 \\ Mx2 & My2 & Mz2 \\ Mx3 & My3 & Mz3 \end{bmatrix} R+T - \begin{bmatrix} Px1 & Py1 & Pz1 \\ Px2 & Py2 & Pz2 \\ Px3 & Py3 & Pz3 \end{bmatrix} = \begin{bmatrix} 0 & 0 & 0 \\ 0 & 0 & 0 \\ 0 & 0 & 0 \end{bmatrix}$$

This forms 9 single equations:

$Mx1 \times Rxx + My1 \times Rxy + Mz1 \times Rxz + x - Px1 = 0$ $Mx1 \times Ryx + My1 \times Ryy + Mz1 \times Ryz + y - Py1 = 0$ $Mx1 \times Rzx + My1 \times Rzy + Mz1 \times Rzz + z - Pz1 = 0$ $Mx2 \times Rxx + My2 \times Rxy + Mz2 \times Rxx + x - Px2 = 0$ $Mx2 \times Ryx + My2 \times Ryy + Mz2 \times Ryz + y - Py2 = 0$ $Mx2 \times Rzx + My2 \times Rzy + Mz2 \times Rzz + z - Pz2 = 0$ $Mx3 \times Rxx + My3 \times Rxy + Mz3 \times Rxz + x - Px3 = 0$ $Mx3 \times Ryx + My3 \times Ryy + Mz3 \times Ryz + y - Py3 = 0$ $Mx3 \times Rzx + My3 \times Rzy + Mz3 \times Rzz + z - Pz3 = 0$

... (*)

with 6 unknowns: $\alpha, \beta, \gamma$, for rotation angles, x, y, z for space translation.

The registration procedure is to find rotation angles $\alpha, \beta, \gamma$ and space translation x, y, z by solving the above 9 equations.

In pseudo-code, the registration procedure is:

```
registration( )
{
    Initialize data buffer;
    Assign fiducial reference points to image data (usually 3 points);
    Initialize magnetic locating system;
    Measure lab positions of the chosen fiducial points;
    Apply equation solving method (non-linear least square)
    on equations(*),
        and find rotation angles α, β, γ and space
        translation x, y, z;
        Form rotation matrix R from α, β, γ and translation matrix
        T from x, y, z;
}
```

The rotation matrix R and translation matrix T can be applied to subsequent positions obtained, including the positions of the of the sensor associated with the catheter.

What is claimed is:

1. Apparatus for determining position comprising:

(a) field generating means for producing a plurality of magnetic fields, each said field having parameters varying with location within a sensing volume according to a known pattern of variation, said patterns of variation being different for different ones of said fields;

(b) at least one sensor adapted to detect one or more of said parameters of said fields generated by said field generating means prevailing at such sensor when said sensor is at an unknown location within said sensing volume and to provide one or more sensor signals representing said one or more parameters;

(c) calculation means for determining a calculated location of said sensor based upon said sensor signals and said known patterns of variation; and (d) feedback control means for adjusting said field generating means to alter said known pattern of variation of at least one of said fields responsive to said sensor signals, said calculated location or both so as to maintain said parameters of each such altered field prevailing at said sensor within a preselected range.

2. Apparatus for determining position comprising:

(a) a plurality of sensors, said sensors being disposed adjacent a sensing volume at different positions, different orientations or both;

(b) field generating means including at least one magnetic field transmitter movable to an unknown location within said sensing volume and adapted to provide at least one magnetic field in said sensing volume, so that the magnetic field from each transmitter varies in according to a known pattern of variation with location relative to such transmitter, said sensors being adapted to detect one or more parameters of the at least one magnetic field provided by said field generating means and to provide said sensor signals representing one or more parameters of the field or fields from said at least one transmitter;

(c) calculation means for determining a calculated location of said at least one transmitter based upon said sensor signals and said known patterns of variation; and (d) feedback control means for adjusting said field generating means to alter said known pattern of variation of at least one of said fields responsive to said sensor signals, said calculated location or both so as to maintain said parameters of each such altered field prevailing at each said sensor within a preselected range.

3. Apparatus as claimed in claim 1 or claim 2 wherein said field generating means is operative to provide DC magnetic fields within said sensing volume.

4. Apparatus as claimed in claim 3 wherein said field generating means includes a plurality of coils and means for intermittently actuating each said coil with a direct current, said feedback control means includes means for altering the magnitude of each said direct current, and wherein said calculation means includes means for sampling the signals from each sensor when a delay time has elapsed after commencement of each said intermittent actuation, said feedback control means further including means for varying the delay time for each actuation in accordance with the magnitude of the current applied in such actuation so as to reduce the delay time when lesser currents are employed and increase the delay time when greater currents are employed.

5. Apparatus as claimed in claim 1 or claim 2 wherein said field generating means is operative to provide AC magnetic fields within said sensing volume.

6. Apparatus as claimed in claim 1 or claim 2 wherein each said sensor has maximum accuracy within a preselected optimum operational range for each said parameter and said preselected range for each said parameter substantially corresponds to said optimum operational range.

7. Apparatus as claimed in claim 1 or claim 2 wherein said preselected range for each said parameter consists of a single value, and wherein said feedback control means is operative to maintain each said parameter of the field at each sensor substantially at said single value.

8. Apparatus as claimed in claim 1 wherein said field generating means includes a plurality of transmitters disposed adjacent said sensing volume.

9. Apparatus as claimed in claim 2 or claim 8 wherein each said transmitter is operative to radiate a field having magnitude decreasing with $r^n$ where r is distance from the transmitter and n is a number greater than 1.

10. Apparatus as claimed in claim 1 further comprising a sensor body, said at least one sensor including a plurality of component sensors disposed on said sensor body, each said component sensor being operative to measure the magnitude of a magnetic field component in a preselected local direction relative to the sensor body.

11. Apparatus as claimed in claim 10 wherein said field generating means includes a plurality of transmitters disposed at spaced-apart locations adjacent said sensing volume, said feedback control means being operative to adjust each said transmitter to transmit a plurality of fields so that for each said field, the magnitude of a component of such field in the local direction of one said component sensor will be within a preselected range.

12. Apparatus as claimed in claim 10 wherein each said component sensor is a Hall effect sensor, a magnetoresistive sensor, a magnetooptical sensor or a flux gate magnetometer.

13. Apparatus as claimed in claim 1 or claim 2 wherein each said sensor includes a coil and wherein said field generating means is arranged to provide AC fields in said sensing volume.

14. Apparatus as claimed in claim 1 wherein said field generating means includes a plurality of transmitters disposed at spaced-apart locations on one side of a reference plane and wherein said sensing volume extends to the other side of said reference plane.

15. Apparatus as claimed in claim 14 wherein said transmitters are disposed substantially in a common plane.

16. Apparatus as claimed in claim 2 wherein said plurality of sensors are disposed at spaced-apart locations on one side of a reference plane and wherein said sensing volume extends to the other side of said reference plane.

17. Apparatus as claimed in claim 16, wherein said sensors are disposed substantially in a common plane.

18. Apparatus as claimed in claim 1 or claim 2 wherein said at least one sensor includes a plurality of sensors, and wherein said sensors can be impaired by exposure to fields having components above a predetermined threshold magnitude, and wherein said feedback control means includes means for controlling said field generating means to assure that no sensor is exposed to a field component having magnitude above its threshold value.

19. Apparatus as claimed in claim 1 or claim 2 wherein said at least one sensor includes a plurality of sensors and wherein said sensors can be impaired by exposure to fields having components above a predetermined threshold magnitude but can be restored after such exposure upon application of a reset routine, said feedback control means including means for initiating such reset routine in the event of such exposure.

20. Apparatus for sensing the disposition of an object in a frame of reference comprising:

(a) transmitter means including at least one transmitter for providing a field;

(b) sensor means including at least one sensor for sensing one or more parameters of a field prevailing at each such sensor, said transmitter means and said sensor means cooperatively defining a plurality of transmitter-sensor pairs, each including one transmitter and one sensor as elements of the pair, one element of each such pair being disposed on the object and the other element of each such pair being disposed at a known disposition in said frame of reference, the sensor means of each such pair being operative to provide sensor signals representing parameters of a field provided by said transmitter means;

(c) calculation means for determining the disposition of said object in said frame of reference based upon said sensor signals; and (d) feedback control means for adjusting said transmitter means responsive to said sensor signals to thereby maintain at least one of said sensor signals within a preselected range.

21. Apparatus for determining position comprising:

(a) a plurality of sensors adapted to detect one or more parameters of a magnetic field prevailing at each such sensor and to provide one or more sensor signals representing said one or more parameters, said sensors being disposed adjacent a sensing volume at different positions, different orientations or both;

(b) field generating means including at least one magnetic field transmitter movable to an unknown location within said sensing volume and adapted to provide at least one magnetic field in said sensing volume, so that the magnetic field from each transmitter varies in according to a known pattern of variation with location relative to such transmitter whereby said sensor signals will represent one or more parameters of the field or fields from said at least one transmitter;

(c) calculation means for determining a calculated location of said at least one transmitter based upon said sensor signals and said known patterns of variation; and (d) feedback control means for adjusting said field generating means to alter said known pattern of variation of at least one of said fields responsive to said sensor signals, said calculated location or both so as to maintain said parameters of each such altered field prevailing at each said sensor within a preselected range, each said transmitter being operative to radiate a field having magnitude substantially equal to $K/r^3$ where r is distance from the transmitter and K is a real number, and wherein said feedback control means is operative to adjust K.

22. Apparatus for determining position comprising:

(a) field generating means for producing a plurality of magnetic fields, each said field having parameters varying with location within a sensing volume according to a known pattern of variation, said patterns of variation being different for different ones of said fields;

(b) at least one sensor adapted to detect one or more of said parameters prevailing at such sensor when said sensor is at an unknown location within said sensing volume and to provide one or more sensor signals representing said one or more parameters;

(c) calculation means for determining a calculated location of said sensor based upon said sensor signals and said known patterns of variation; and (d) feedback control means for adjusting said field generating means to alter said known pattern of variation of at least one of said fields responsive to said sensor signals, said calculated location or both so as to maintain said parameters of each such altered field prevailing at said sensor within a preselected range, said field generating means including a plurality of transmitters disposed adjacent said sensing volume, each said transmitter being operative to radiate a field having magnitude substantially equal to $K/r^3$ where r is distance from the transmitter and K is a real number, and wherein said feedback control means is operative to adjust K.

\* \* \* \* \*

UNITED STATES PATENT AND TRADEMARK OFFICE
CERTIFICATE OF CORRECTION

PATENT NO. : 5,729,129

DATED : March 17, 1998

INVENTOR(S) : Acker

It is certified that error appears in the above-identified patent and that said Letters Patent is hereby corrected as shown below:

Column 4, line 25, "or in a" should read --or in an--.

Column 4, line 65, "prospective" should read --perspective--.

Column 5, line 1, "prospective" should read --perspective--.

Column 5, line 6, after "invention." insert new paragraph.

Column 5, line 30, "$X^1$, $Y^1_j$ and $A^1$" should read --$X^1$, $Y^1$ and $Z^1$--.

Column 5, line 58, "ND" should read --A/D--.

Column 6, line 13, delete "[MOVE THIS UP].".

Column 6, line 29, delete "sensitive to magnetic field directed in direc-".

Column 6, line 30, delete "tion $X^1$, but largely insensitive to".

Column 6, line 51, "invention, an" should read --invention, a--.

Column 7, line 41, "range, than" should read --range, then--.

Column 9, line 29, "probe example," should read --probe 14. For example,--.

Column 10, line 13, "ignore" should read --ignored--.

Column 10, line 31, "sensor" should read --sensors--.

UNITED STATES PATENT AND TRADEMARK OFFICE
CERTIFICATE OF CORRECTION

PATENT NO. : 5,729,129
DATED : March 17, 1998
INVENTOR(S) : Acker

It is certified that error appears in the above-indentified patent and that said Letters Patent is hereby corrected as shown below:

Column 10, line 32, "sensor" should read --sensors--.

Column 11, line 40, "respect the" should read --respect to the--.

Column 13, line 9, "with a transmitters" should read --with transmitters--.

Column 14, line 6, "tracking a an" should read --tracking an--.

Column 14, line 65, " $T_{[i][j]} = e_{\pi(i)} \cdot e_{\pi(j)} \ \forall i,j \in \{1,2,3\}$ " should read
-- $T_{[i][j]} = e_{\pi(i)} \cdot e_{\pi(j)} \quad \forall i,j \in \{1,2,3\}$ --.

Column 15, line 1, " $ortho\_OV_{[i][j]} = e_{\pi(i)} \cdot e_{\pi(j)} \ \forall i,j \in \{1,2,3\}$ " should read
-- $ortho\_OV_{[i][j]} = e_{\pi(i)} \cdot e_{\pi(j)} \quad \forall i,j \in \{1,2,3\}$ --.

UNITED STATES PATENT AND TRADEMARK OFFICE
CERTIFICATE OF CORRECTION

PATENT NO. : 5,729,129
DATED : March 17, 1998
INVENTOR(S) : Acker

It is certified that error appears in the above-indentified patent and that said Letters Patent is hereby corrected as shown below:

Column 15, line 5, "cos ($\beta$)" should read --cos ($\gamma$)--.

Column 15, line 27, " $e_{\eta(i)}$ " should read --$e_{\eta(i)}$--.

Column 17, line 20, " $Mx2 \times Rxx + My2 \times Rxy + Mz2 \times Rxx + x - Px2 = 0$ "
should read -- $Mx2 \times Rxx + My2 \times Rxy + Mz2 \times Rxz + x - Px2 = 0$ --.

Column 17, line 53, delete the second occurrence of "of the".

Signed and Sealed this

Eighteenth Day of August, 1998

Attest:

BRUCE LEHMAN

Attesting Officer — Commissioner of Patents and Trademarks